United States Patent

Rogers et al.

[11] Patent Number: 5,113,585
[45] Date of Patent: May 19, 1992

[54] SHAVING SYSTEM

[75] Inventors: Brian A. Rogers, South Boston; Mingchih M. Tseng, Hingham, both of Mass.

[73] Assignee: The Gillette Company, Boston, Mass.

[21] Appl. No.: 589,678

[22] Filed: Sep. 28, 1990

[51] Int. Cl.⁵ .................. B26B 19/40; B26B 21/14; B26B 21/40
[52] U.S. Cl. .......................... 30/41; 30/50; 30/90
[58] Field of Search ............. 30/41, 50, 40, 32, 84, 30/85, 86

[56] References Cited

U.S. PATENT DOCUMENTS

| 4,170,821 | 10/1979 | Booth |  |
|---|---|---|---|
| 4,381,293 | 4/1983 | Michel | 30/90 |
| 4,586,255 | 5/1986 | Jacobson |  |
| 4,624,051 | 11/1986 | Apprille, Jr. et al. | 30/50 |
| 4,850,106 | 7/1989 | Braun et al. | 30/41 |
| 4,858,314 | 8/1989 | Cunningham | 30/41 |
| 4,872,263 | 10/1989 | Etheredge | 30/41 |
| 4,875,287 | 10/1989 | Creasy |  |

FOREIGN PATENT DOCUMENTS 2024082  5/1982  United Kingdom .

Primary Examiner—Douglas D. Watts
Assistant Examiner—Paul M. Heyrana, Sr.
Attorney, Agent, or Firm—Fish & Richardson

[57] ABSTRACT

A shaving unit comprises at least one blade and a shaving composite that has a surface for engaging the user's skin adjacent the blade edge. The shaving unit may be of a disposable cartridge type adapted for coupling to and uncoupling from a razor handle or may be integral with a handle so that the complete razor is discarded as a unit when the blade or blades become dulled. The blade edge (or edges) cooperate with skin engaging surfaces to define shaving geometry. The shaving aid composite is a mixture of water insoluble matrix material, an effective amount of shaving aid material, and a water soluble low molecular weight release enhancing agent that enhances the releasability of the shaving aid material from the matrix material.

12 Claims, 1 Drawing Sheet

SHAVING SYSTEM

This invention relates to shaving systems, and more particularly to shaving systems of the wet shave type.

In shaving systems of the wet shave type, factors such as the frictional drag of the razor across the skin, the force needed to sever hairs, and irritation of preexisting skin damage can create a degree of shaving discomfort. Discomfort, and other problems accompanying wet shaving systems, can be alleviated by the application of shaving aids to the skin. Shaving aids may be applied prior to, during, or after shaving. A number of problems accompany the use of pre- and post-applied shaving aids. Pre-applied-shaving aids can evaporate or can be carried away from the site of application by repeated strokes of the razor. Post-applied-shaving aids are not present on the skin during shaving and thus their application may be to late to prevent an unwanted affect. Both pre-applied and post-applied shaving aids add additional steps to the shaving process.

Proposals have been made to incorporate a shaving aid e.g., lubricant, whisker softener, razor cleanser, medicinal agent, cosmetic agent or combination thereof, into a razor, e.g., by depositing a shaving aid in a recess on the razor, by incorporating a shaving aid directly into one or more molded polymeric components of the razor, by adhesively securing a shaving aid composite to the razor, and by use of a mechanical connection between a shaving aid composite and the razor. A water-soluble shaving aid, e.g. polyethylene oxide, has been mixed with non-water-soluble material, e.g., a polystyrene polymer, to form an insoluble polymer/soluble shaving aid composite. The composite has been mounted on razor and shaving cartridge structures, adjacent the shaving edge or edges, of single or multiple blade shaving system. Upon exposure to water, the water-soluble shaving aid leaches from the composite onto the skin.

Extruded composites with relatively large amounts of shaving agent material (up to 80% by weight) and relatively low amounts of water insoluble matrix material (as little as 20% by weight) are relatively weak and have a tendency towards mechanical failure, both in assembly and in use. Increase in mechanical strength can be obtained with increased amounts of the matrix material. However, such increase reduces the releasability of the shaving material.

In accordance with one aspect of the invention, there is provided a shaving unit that comprises at least one blade and a shaving composite that has a surface for engaging the user's skin adjacent the blade edge. The shaving unit may be of a disposable cartridge type adapted for coupling to and uncoupling from a razor handle or may be integral with a handle so that the complete razor is discarded as a unit when the blade or blades become dulled. The blade edge (or edges) cooperate with skin engaging surfaces to define shaving geometry. The shaving aid composite is a mixture of water insoluble matrix material, an effective amount of shaving aid material, and a water soluble low molecular weight release enhancing agent that enhances the releasability of the shaving aid material from the matrix material.

Preferably, the composite includes 20-60 percent by weight of the water-insoluble matrix material, 20-75 percent by weight of the shaving aid material, and 5-20 percent by weight of the release enhancing agent. Suitable water-insoluble matrix materials include, for example, polyethylene, polypropylene, polystyrene and polyacetyl. Suitable release-enhancing agents include, for example, polyethylene glycol, methoxypolyethylene glycol, methylcellulose, and carboxypolymethylene. Suitable shaving aid materials include, for example, polyethylene oxide, polyvinyl pyrrolidone, polyacrylamide, hydroxypropyl cellulose, polyvinyl imidazonline, polyhydroxyethylmethacrylate, silicone copolymers, sucrose stearate, vitamin E, panthenol, aloe and essential oils such as menthol.

In particular embodiments, the shaving agent composite is a member of extrusion-oriented blend of polymeric materials that contains water-soluble and water-insoluble materials, the nature and relative proportions of the water-soluble and water-insoluble polymeric materials being such that the member has adequate mechanical strength, both as initially produced and after a significant amount of the water-soluble material has been leached out, the quantity of the water-soluble material being sufficient to provide effective shaving assistance, such as lubrication, for the entire expected life of the blade or blades. Preferably, the molecular weight of the release enhancing agent is less than five percent of the average molecular weight of the shaving aid material.

In a particular embodiment, the release-enhancing agent is polyethylene glycol of about 4,500 molecular weight and the shaving aid material is polyethylene oxide of at least about one million molecular weight.

Other features and advantages will be seen as the following description of particular embodiments progresses, in conjunction with the drawings, in which.

DESCRIPTION OF PARTICULAR EMBODIMENTS

Figure 1:
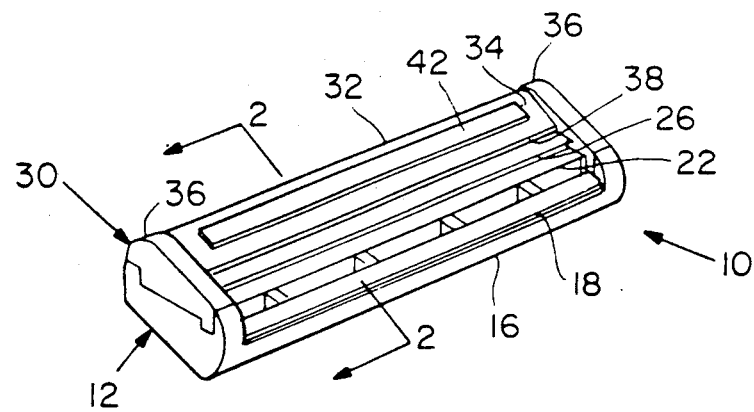
FIG. 1 is a perspective view of a razor unit in accordance with the invention.
Figure 2:
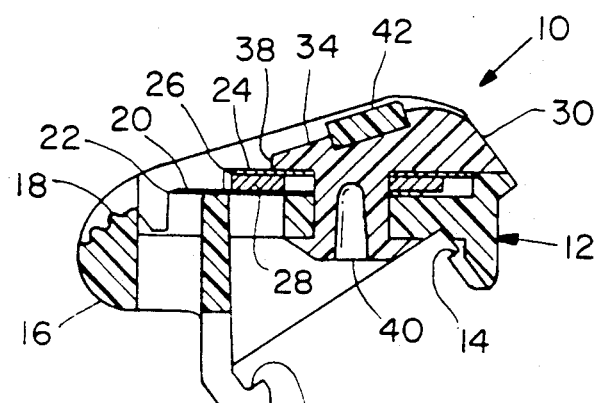
FIG. 2 is a sectional view taken along the line 2—2 of FIG. 1.

The shaving unit 10 shown in FIGS. 1 and 2 includes base or platform member 12 molded of high impact polystyrene that includes integral coupling groove structure 14 for attachment to a razor handle and guard structure 16 that defines a transversely extending forward skin engaging surface 18. On the upper surface of platform 12 are disposed steel leading blade 20 having a sharpened edge 22, steel following blade 24 having sharpened edge 26, and aluminum spacer member 28 that maintains blades 20 and 24 in spaced relation. Cap member 30 is molded of high impact polystyrene and has body portion 32 that defines skin engaging surface 34 that extends transversely between forwardly projecting end walls 36 and has a front edge 38 that is disposed rearwardly of blade edge 26. Integral rivet portions 40 extend downwardly from transversely extending body portion 32 and pass through holes in blades 20 and 24, spacer 28, and platform 12 to secure cap 30, blades 20, 24 and spacer 28 on platform 12. Adhesively affixed to skin engaging surface 34 is shaving aid composite 42.

Figure 3:
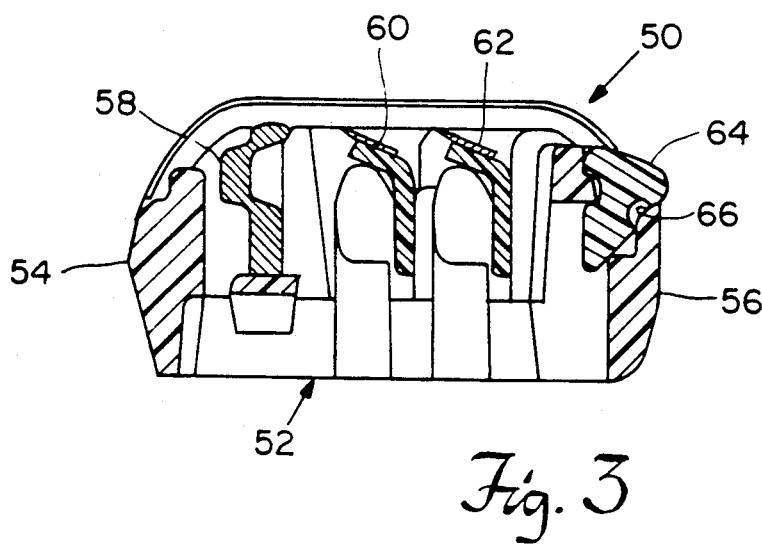
FIG. 3 is a perspective view of another razor unit in accordance with the invention.

The shaving unit 50 shown in FIG. 3 is of the type shown in Jacobson U.S. Pat. No. 4,586,255 and includes body 52 with front portion 54 and rear portion 56. Resiliently secured in body 52 are guard member 58, leading blade unit 60 and trailing blade unit 62. A shaving aid composite in the form of elongated insert member 64 is frictionally locked in opening 66 of rear portion 56.

The following examples show by way of illustration and not by way of limitation practice of the invention.

EXAMPLE 1

Insert members 42 and 64 are formed of a blend of 55% by weight of a water-soluble polymer (specifically a mixture of sixty weight percent Polyox Coagulant polyethylene oxide—5,000,000 molecular weight—and forty weight percent Polyox WSN—750 polyethylene oxide—300,000 molecular weight), 35% by weight of water-insoluble high impact polystyrene, and 10% by weight of water-soluble polyethylene glycol (4500 molecular weight). The blend includes color dye and bactericide additives in minor amounts. The blend is extruded through an extruder with a barrel pressure of about 1800 psi and a temperature of about 180° C. and a die pressure of about 2400 psi and a temperature of about 185° C. to form an extruded strip member of cross-sectional shape indicated in FIG. 3. Members 64 are sliced from the extruded strip and secured in openings 66 of shaving units 50. A strip of cross-sectional shape indicated in FIG. 2 is similarly extruded and sliced into members 42 that are adhesively secured in a recess in cap member 30. The resulting extruded members are sturdy and have attractive appearance, and the resulting cartridges possess good overall shaving performance.

Immersion of member 64 in water causes gradual release of the polyethylene oxide, the loss of weight of member 64 due to release of polyethylene oxide being a generally linear function of time—member 64 having about two percent weight loss after immersion in 20°-23° C. water for thirty minutes and about twenty percent weight loss after immersion in 20°-23° C. water for two hundred ten minutes (the weight loss in each instance being measured after the member 64 has been dried in the air at 50° C. for twenty-four hours).

EXAMPLE 2

Insert members 64 are formed of a blend of 60% by weight of a water-soluble polymer (specifically a mixture of sixty weight percent Polyox Coagulant polyethylene oxide—5,000,000 molecular weight—and forty weight percent Polyox WSN—750 polyethylene oxide—300,000 molecular weight), 35% by weight of water-insoluble high impact polystyrene, and 5% by weight of water-soluble polyethylene glycol (8,000 molecular weight). The blend includes color dye and bactericide additives in minor amounts. The blend is extruded through an extruder with a barrel pressure of about 1800 psi and a temperature of about 180° C. and a die pressure of about 2400 psi and a temperature of about 185° C. to form an extruded strip member of cross-sectional shape indicated in FIG. 3. Members 64 are sliced from the extruded strip and secured in openings 66 of shaving units 50. The resulting extruded members are sturdy and have attractive appearance, and the resulting cartridges possess good overall shaving performance.

EXAMPLE 3

Insert members 64 are formed of a blend of 55% by weight of a water-soluble polymer (specifically a mixture of sixty weight percent Polyox Coagulant polyethylene oxide—5,000,000 molecular weight—and forty weight percent Polyox WSN—750 polyethylene oxide—300,000 molecular weight), 35% by weight of water-insoluble high impact polystyrene, and 10% by weight of water-soluble polyethylene glycol (20,000 molecular weight). The blend includes color dye and bactericide additives in minor amounts. The blend is extruded through an extruder with a barrel pressure of about 1800 psi and a temperature of about 180° C. and a die pressure of about 2400 psi and a temperature of about 185° C. to form an extruded strip member of cross-sectional shape indicated in FIG. 3. Members 64 are sliced from the extruded strip and secured in openings 66 of shaving units 50. The resulting extruded members are sturdy and have attractive appearance, and the resulting cartridges possess good overall shaving performance.

EXAMPLE 4

Insert members 64 are formed of a blend of 60% by weight of a water-soluble polymer (specifically a mixture of sixty weight percent Polyox Coagulant polyethylene oxide—5,000,000 molecular weight—and forty weight percent Polyox WSN—750 polyethylene oxide—300,000 molecular weight), 30% by weight of water-insoluble high impact polystyrene, and 10% by weight of water-soluble polyethylene glycol (4500 molecular weight). The blend includes color dye and bactericide additives in minor amounts. The blend is extruded through an extruder with a barrel pressure of about 1800 psi and a temperature of about 180° C. and a die pressure of about 2400 psi and a temperature of about 185° C. to form an extruded strip member of cross-sectional shape indicated in FIG. 3. Members 64 are sliced from the extruded strip and secured in openings 66 of shaving units 50. The resulting extruded members are sturdy and have attractive appearance, and the resulting cartridges possess good overall shaving performance.

While particular embodiments of the invention have been shown and described, various modifications will be apparent to those skilled in the art and therefore it is not intended that the invention be limited to the disclosed embodiment or to details thereof and departures may be made therefrom within the spirit and scope of the invention.

What is claimed is:

1. A shaving system of the wet shave type comprising a blade member, and structure defining an external skin engaging portion adjacent the shaving edge of the said blade member, said skin engaging portion including a shaving aid composite of extrusion-oriented material that includes a matrix of water-insoluble polymeric material selected from the group consisting of polyethylene, polypropylene, polystyrene, and polyacetyl, an effective amount of a water-leachable shaving aid material selected from the group consisting of polyethylene oxide, polyvinyl pyrrolidone, polyacrylamide, hydroxypropyl cellulose, polyvinyl imidazonline, polyhydroxyethylmethacrylate, silicone polymers, sucrose stearate, vitamin E, Panthenol, aloe, and essential oils, and a low molecular weight release-enhancing agent selected from the group consisting of polyethylene glycol, methoxypolyethylene glycol, methylcellulose, and carboxypolymethylene.

2. The shaving system of claim 1 wherein said shaving aid composite comprises 20-60% by weight of said matrix material, 20-75% by weight of said water-leachable shaving aid material, and 5-20% by weight of said release-enhancing agent.

3. The shaving system of claim 1 wherein the molecular weight of said release-enhancing agent is less than about 20,000 and the molecular weight of said shaving aid material is at least about one million.

4. The shaving system of claim 1 wherein the release of said shaving aid material is a generally linear function of time over the entire expected life of the shaving system.

5. The shaving system of claim 4 wherein the molecular weight of said release-enhancing agent is less than five percent of the average molecular weight of said shaving aid material.

6. The shaving system of claim 1 wherein said shaving aid composite comprises about 35% by weight of said matrix material, about 55% by weight of said water-leachable shaving aid material, and about 10% by weight of said release-enhancing agent.

7. The shaving system of claim 6 wherein said polymeric matrix material is high impact polystyrene; said shaving aid material includes polyethylene oxide; and said release-enhancing agent is polyethylene glycol.

8. The shaving system of claim 7 wherein the release of said shaving aid material is a generally linear function of time over the entire expected life of the shaving system.

9. A shaving system of the wet shave type comprising two blade members that have parallel spaced transversely extending cutting edges, structure defining an external skin engaging surface portion forward of the cutting edges of said blade members, structure defining an external skin-engaging surface rearwardly of the cutting edges of said blade members, and a shaving aid member of extrusion-oriented material that includes a matrix of water-insoluble polymeric material selected from the group consisting of polyethylene, polypropylene, polystyrene, and polyacetyl, an effective amount of a water-leachable shaving aid material selected from the group consisting of polyethylene oxide, polyvinyl pyrrolidone, polyacrylamide, hydroxypropyl cellulose, polyvinyl imidazonline, polyhydroxyethylmethacrylate, silicone polymers, sucrose stearate, vitamin E, Panthenol, aloe, and essential oils, and a low molecular weight release-enhancing agent secured to one of said skin-engaging surface portions.

10. The shaving system of claim 9 wherein said shaving aid member comprises about 35% by weight of said matrix material, about 55% by weight of said water-leachable shaving aid material, and about 10% by weight of said release-enhancing agent.

11. The shaving system of claim 10 wherein said polymeric matrix material is high impact polystyrene; said shaving aid material includes polyethylene oxide; and said release-enhancing agent is polyethylene glycol.

12. The shaving system of claim 11 wherein the molecular weight of said release-enhancing agent is less than about twenty thousand and the molecular weight of said shaving aid material is at least about one million.

* * * * *